US010758559B1

United States Patent

Nair

(12) United States Patent
(10) Patent No.: US 10,758,559 B1
(45) Date of Patent: Sep. 1, 2020

(54) TARGETING CATHEPSIN K TO FACILITATE WOUND HEALING

(71) Applicant: University of Wyoming, Laramie, WY (US)

(72) Inventor: Sreejayan Nair, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 16/121,443

(22) Filed: Sep. 4, 2018

Related U.S. Application Data

(60) Provisional application No. 62/553,702, filed on Sep. 1, 2017.

(51) Int. Cl.

| | |
|---|---|
| ***A61K 31/7105*** | (2006.01) |
| ***A61P 17/02*** | (2006.01) |
| ***A61K 9/00*** | (2006.01) |
| ***A61L 26/00*** | (2006.01) |

(52) U.S. Cl.
CPC ........ *A61K 31/7105* (2013.01); *A61K 9/0014* (2013.01); *A61L 26/0009* (2013.01); *A61L 26/0061* (2013.01); *A61P 17/02* (2018.01)

(58) Field of Classification Search
CPC .. A61K 31/7105; A01K 2207/05; A61P 17/02
See application file for complete search history.

(56) References Cited

U.S. PATENT DOCUMENTS

| | | | | |
|---|---|---|---|---|
| 5,457,093 | A | 10/1995 | Cini et al. | |
| 9,833,498 | B2 | 12/2017 | Keller et al. | |
| 9,873,668 | B2 | 1/2018 | Chaplin et al. | |
| 9,943,522 | B2 | 4/2018 | Golz et al. | |
| 10,005,823 | B2 | 6/2018 | Lin et al. | |
| 10,034,826 | B2 | 7/2018 | Idkowiak-Baldys et al. | |
| 10,045,950 | B2 | 8/2018 | Tsai et al. | |
| 10,058,633 | B2 | 8/2018 | Ferrari et al. | |
| 2003/0003157 | A1 | 1/2003 | Ohan et al. | |
| 2006/0111440 | A1* | 5/2006 | Gauthier | C07C 255/46 514/519 |
| 2007/0258952 | A1* | 11/2007 | Tong | C12N 7/00 424/93.2 |
| 2008/0125442 | A1* | 5/2008 | Percival | A61K 31/00 514/255.03 |
| 2008/0138277 | A1* | 6/2008 | Epstein | G06F 1/1626 424/1.61 |
| 2009/0111771 | A1* | 4/2009 | Cullis-Hill | A61K 31/7024 514/54 |
| 2014/0271609 | A1 | 9/2014 | Keller et al. | |
| 2015/0352064 | A1 | 12/2015 | Bitar et al. | |
| 2016/0186259 | A1* | 6/2016 | Ofir | C12Q 1/6881 435/325 |

OTHER PUBLICATIONS

Runger et al. Journal of Investigative Dermatology 127, 293-297 (Year: 2007).*
Drake et al. Endocrine Reviews 38: 325-350 (Year: 2017).*
Sharma et al. Biochem. J, 465, 163-173 (Year: 2005).*
Sreejayan Nair, et al., "Targeting Cathepsin K to Facilitate Diabetic Wound Healing", presentation at Wyoming Sensory Biology Symposium, Sep. 2018.
Sreejayan Nair, et al., "Targeting Cathepsin K to Promoted Diabetic Wound Healing", The FASEB Journal vol. 31 No. 1 Supplement 673.11, Apr. 2017.
George Han, and Roger Ceilley, "Chronic Wound Healing: A Review of Current Management and Treatments", Adv. Ther. vol. 34, pp. 599-610, Jan. 2017.
Ming Gao, et al., "Acceleration of diabetic wound healing using a novel protease-anti-protease combination therapy", Proc. Natl. Acad. Sci., vol. 112(49) pp. 15226-15231, Dec. 2015.
Sara McCarty, and Steven Percival, "Proteases and Delayed Wound Healing, Advances in Wound Care", vol. 2, No. 8, pp. 438-447, Oct. 2013.
Toshitake Hirai et al., "Cathepsin K Is Involved in Development of Psoriasis-like Skin Lesions through TLR-Dependent Th17 Activation", J Immunol 2013; vol. 190, pp. 4805-4811, Prepublished online Mar. 29, 2013.
Dieter Bromme, and Fabian Lecaille, "Cathepsin K inhibitors for osteoporosis and potential off-target effects", Expert Opin Investig Drugs; vol. 18(5), pp. 585-600, May 2009.
Richard Clark et al., "Tissue Engineering for Cutaneous Wounds", Journal of Investigative Dermatology, vol. 127, issue 5, pp. 1018-1029, May 2007.

* cited by examiner

*Primary Examiner* — Brian Whiteman
(74) *Attorney, Agent, or Firm* — MacMillan, Sobanski & Todd, LLC

(57) ABSTRACT

Diabetic wounds have elevated levels of cathepsin K, a protease enzyme, which degrades proteins, such as collagen, causing delayed wound healing. By targeting cathepsin K, diabetic wound healing is ameliorated. Methods and devices for treatment include topical application of pharmacological inhibitors of cathepsin K, for example, in the form of gel, powder, or bandage. Other methods and systems include localized genetic knock out of the cathepsin K gene by topical application of a small interfering RNA (siRNA) or antisense oligonucleotide to aid in wound healing.

13 Claims, 5 Drawing Sheets
(4 of 5 Drawing Sheet(s) Filed in Color)

TARGETING CATHEPSIN K TO FACILITATE WOUND HEALING

CROSS-REFERENCE TO RELATED APPLICATIONS

This application claims priority to U.S. Provisional Patent Application No. 62/553,702, entitled: "Targeting Cathepsin K to Facilitate Wound Healing," filed Sep. 1, 2017, the entire disclosure of which is expressly incorporated herein by reference.

STATEMENT REGARDING FEDERALLY SPONSORED RESEARCH

This invention was made with government support under Grant No. #2P20GM103432, awarded by the National Institutes of Health. The government has certain rights in the invention.

BACKGROUND

Non-healing wounds are a serious complication of diabetes mellitus. Effective treatment of diabetic wounds and related conditions is aided by understanding the pathophysiology and cellular signaling pathways causing the disease and its effects. Research into molecules that can function to inhibit or augment such pathways has shown promise for the treatment of diabetes. However, despite advances in research, there are few options for treating non-healing diabetic wounds. Thus, there is a need for methods and compositions to ameliorate and treat wounds in diabetic subjects.

SUMMARY

Compositions, structures, and methods for use in wound healing, by modulating cathepsin K, are provided herein. The features provided by the embodiments described will be more fully understood in view of the following detailed description, in conjunction with the drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

The embodiments set forth in the drawings are illustrative and exemplary in nature and not intended to limit the subject matter defined by the claims. The following detailed description of the illustrative embodiments can be understood when read in conjunction with the following drawings.

DETAILED DESCRIPTION

Figure 1A:
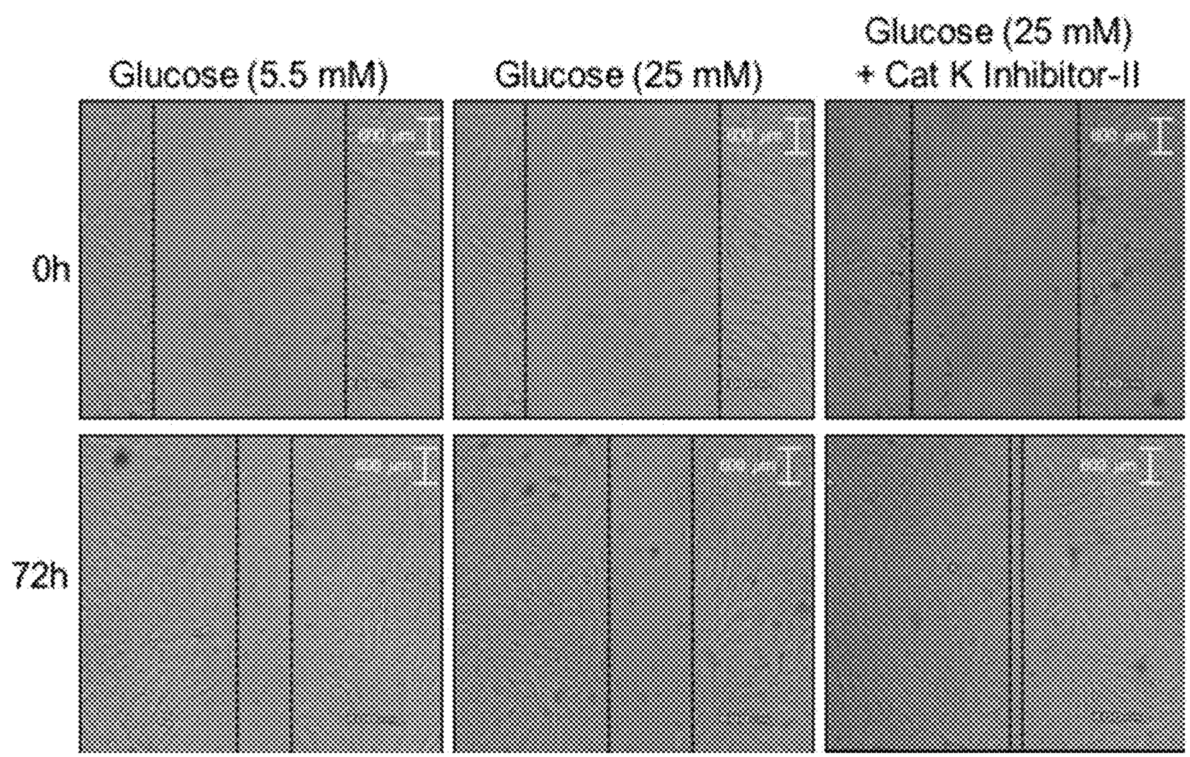
FIG. 1A shows images from a monolayer wound-healing assay comparing treatment groups.

Wound healing is a complex process comprising a variety of cells and mediators that progresses through a cascade of events involving inflammation, proliferation, angiogenesis, and remodeling.

Persistently elevated protease activity in chronic wounds impedes wound healing. Chronic wounds fail to proceed through the normal phases of wound healing in an orderly and timely manner. Often, chronic wounds stall in the inflammation phase of healing.

During the normal healing process in acute wounds, proteases are tightly regulated by their inhibitors. The cysteine protease cathepsin K is the most potent collagenolytic and elastolytic enzyme in the mammalian species. Collagen, the primary substrate for cathepsin K, plays a critical role in wound healing by facilitating the migration of dermal fibroblasts and keratinocytes and by stimulating vascularization, and granulation tissue formation.

The healing of wounds is a highly orchestrated biological process that involves a complex interplay between extracellular matrix (ECM), skin cells and growth factors. Proteases regulate the balance between ECM degradation and deposition, which creates an equilibrium necessary for the timely and coordinated healing of cutaneous wounds. This balance is disrupted in wounds that poorly heal. ECM provides structure and support to cells and facilitates cell signaling that leads to migration, proliferation and collagen synthesis. The most abundant protein in the ECM is collagen, which forms fibers that provide tensile strength to the wound. Type-1 dermal collagen enhances migration of keratinocytes, fibroblasts and endothelial cells, which play a pivotal role in wound re-epithelization, fibroplasia and neo-angiogenesis.

The development of chronic diabetic wounds is characterized by a highly proteolytic microenvironment or 'catabolic state'. The elevated proteolytic activity leads to a continuous breakdown of the extracellular matrix proteins, sustaining a prolonged destructive state that delays wound healing. Collagen is the major extracellular matrix protein which plays a critical role in wound healing and is a major target for proteolysis.

In chronic wounds, protease levels may exceed levels controlled by their respective inhibitors, leading to destruction of extracellular matrix (ECM) and degradation of growth factors and their receptors. The proteolytic destruction of the ECM, including collagen, delays or prevents the wound from moving into the proliferative phase and also attracts more inflammatory cells, further perpetuating the inflammation cycle.

Collagen is involved in all aspects of wound healing including cell differentiation, migration and granulation tissue formation. Although collagen turnover in normal connective tissue is a very slow and controlled process, in chronic nonhealing wounds, the extent of collagen degradation can be extensive, due to the upregulation of proteolytic enzymes that degrade collagen.

Consequently, increased protease levels and decreased collagen levels lead to impaired wound repair in diabetic subjects and animal models of diabetes.

Delayed or impaired wound healing is a severe complication of diabetes often leading to lower limb amputations and diminished quality of life. Non-healing wounds affect about a quarter of people with diabetes and represents a primary cause of about 85% of lower limb amputations. Wounds with enhanced protease activity have a 90% probability that they will not heal without intervention.

Diabetic wounds do not frequently respond to standard wound care such as debridement, compression, moisture balance, and control of bacterial burden. Therefore, successful treatment can instead be directed to correcting underlying biochemical defects.

Cathepsin K is upregulated in the diabetic skin wounds. Excessive cathepsin activity in humans has been associated with osteoporosis, arthritis, and certain bone cancers. As described herein, inhibition of cathepsin K in diabetic wounds facilitates wound healing.

Methods, systems, and compounds are described for inhibiting cathepsin K, a potent protease, in diabetic wounds to aid healing.

EXAMPLES

Example 1: Pharmacological Inhibition of Cathepsin K Promotes Fibroblast Migration In Vitro Referring now to FIGS. 1A-1B, the in vitro monolayer wound-healing assay mimics cell migration during wound healing. An in vitro monolayer wound-healing assay in cultured human fibroblasts was used to test whether pharmacological inhibition of cathepsin K affected cell migration under high-glucose (25 mM) conditions. Mannitol was included to control for osmotic pressure and hydroxyurea to eliminate the potential effects of cell proliferation.

Figure 1B:
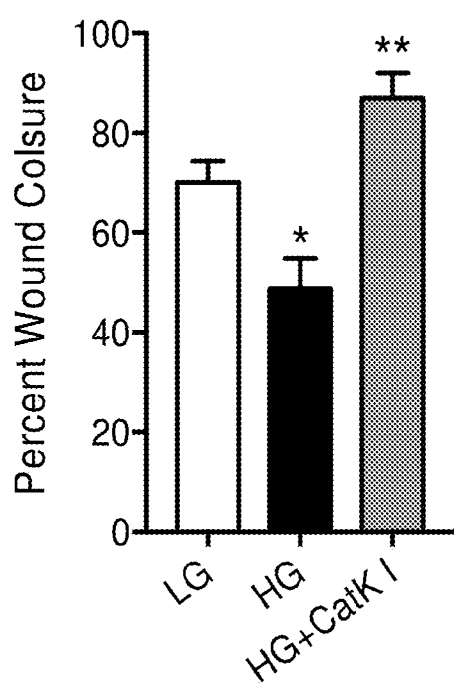
FIG. 1B shows a graph comparing percentage of monolayer wound closure by treatment group.

Cultured fibroblasts, subjected to a high-glucose media, exhibited impaired migration and re-epithelization, as compared to those grown in a normal-glucose (5.5 mM) media. Presence of Boc-I, 1-(N-Benzyloxycarbonyl-leucyl)-5-(N-Boc-phenylalanyl-leucyl) carbohydrazide, Z-L-NHN-HCONHNH-LF-Boc), henceforth referred to as cathepsin K inhibitor II), not only reconciled the effects of high glucose, but also increased migration beyond that observed in the cells treated with a low-glucose media, as shown in FIGS. 1A-1B, indicating that inhibition of cathepsin K facilitates epithelization and wound healing under high-glucose conditions.

Referring again to FIGS. 1A-1B, inhibition of cathepsin reverses the inhibitory effect of high glucose (HG) on cell migration in a monolayer wound-healing assay. Confluent human fibroblasts were serum starved and subjected to a media containing low (5 mM, LG) or high (25 mM, HG) glucose. The cell monolayer was wounded with a linear scratch using a sterile pipette tip and treated with 100 ng/ml of cathepsin K inhibitor-II in the presence of 5 μg/ml hydroxyurea. At 0 time (upper left panel) and 72 h (lower left panel) after wounding, the cells were photographed using an inverted microscope equipped with a digital camera. Scale bar=600 μm. FIG. 1A. Representative phase-contrast images for each treatment group. FIG. 1B. Bar graph represents the percentage wound closure 72 h after wounding as measured using the NIH Image J software and represented as mean±SEM, n=6, *p<0.01 compared to LG; **p<0.05 compared to LG.

Figure 2A:
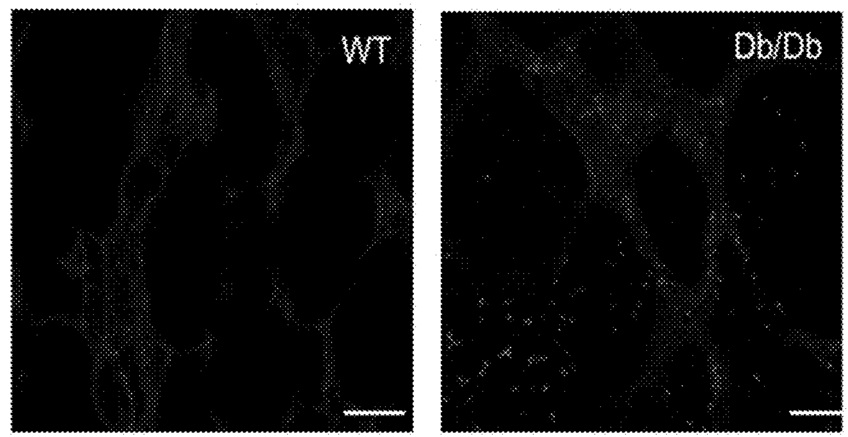
FIG. 2A depicts representative immunostaining of cathepsin K in skin tissues for wild-type (WT) and db/db mice 3d following wounding.
Figure 2B:
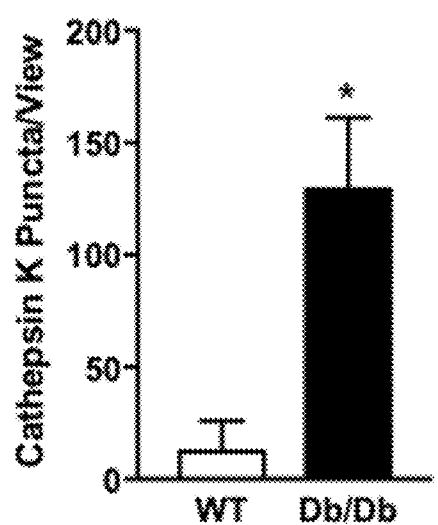
FIG. 2B shows a bar graph comparing protein levels of cathepsin K in wounds in wild-type and diabetic mouse models.
Figure 2C:
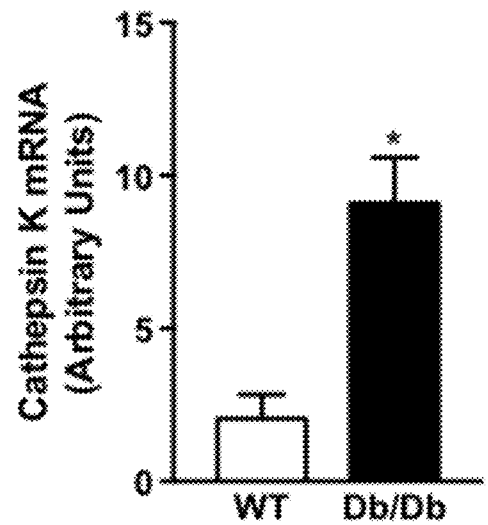
FIG. 2C shows Cathepsin K mRNA levels from WT and db/db mice.

Example 2: Cathepsin K mRNA and Protein Levels are Elevated in the Diabetic Wound Referring to FIGS. 2A-2C the expression levels of cathepsin K were investigated in wounds from wild-type and leptin receptor-deficient diabetic (db/db) mice—an established model of deficient wound-healing associated with diabetes. Consistent with previous studies with scar tissue in the skin, cathepsin K protein and mRNA levels were significantly higher in the wound tissue of db/db mice compared to its wild-type (WT) littermates as evidenced in the immunohistochemical images (FIGS. 2A-C). The results were verified by an independent laboratory.

Constitutive expression of cathepsin K was weak in uninvolved skin from diabetic mice (data not shown). Consistent with the protein levels, a robust elevation in cathepsin K mRNA levels was observed in the wound tissue of db/db mice compared to the wild type. These data indicate a diabetes-associated dysregulation of cathepsin K protein levels in the skin wound and show that cathepsin K is upregulated in the diabetic wound. The data presented in FIGS. 2A-2C is from skin tissues taken on the 5th day following injury. Qualitatively similar data were obtained from tissues obtained 12 days' post injury.

Referring again to FIGS. 2A-2C, Cathepsin K is elevated in wound tissues from diabetic (db/db) mice. FIG. A. Representative immunostaining of cathepsin K in skin tissues five days following wounding. Scale bar 2 μm. FIG. B. Quantification of cathepsin positive puncta per high power field, and FIG. C. Cathepsin K. mRNA levels in 3-day-old wound tissue from wild-type (WT) and db/db mice. Data in the bar graphs are expressed as mean±SEM, n=6, *p<0.001.

Figure 3A:
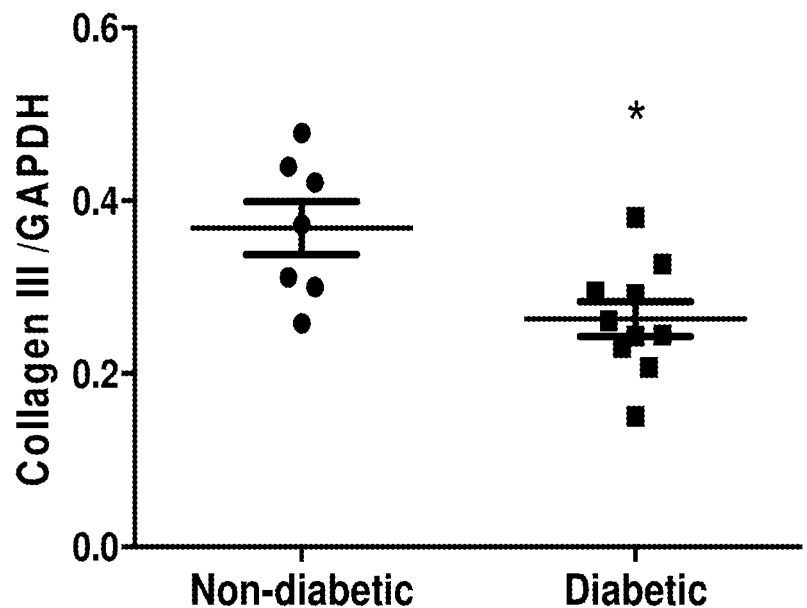
FIG. 3A depicts protein expression levels for collagen in human skin from non-diabetic and diabetic subjects.
Figure 3B:
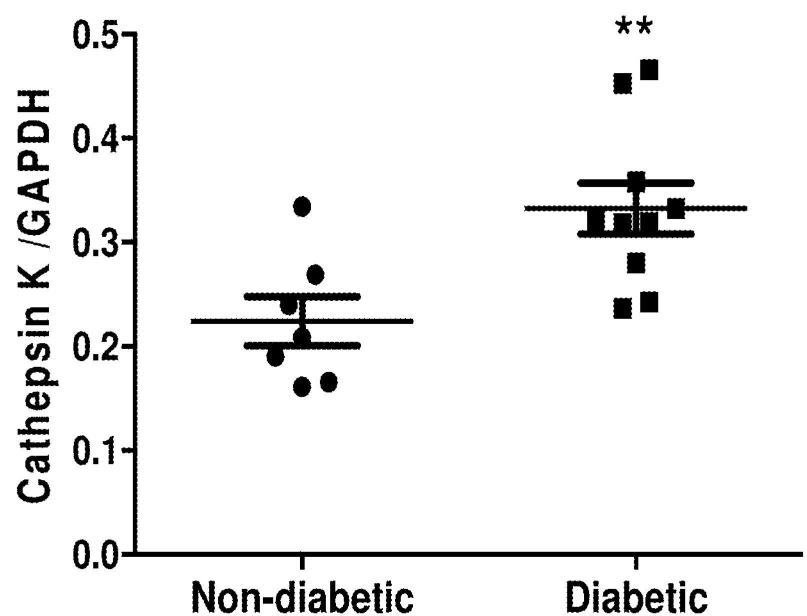
FIG. 3B depicts protein expression levels for Cathepsin K in human skin from non-diabetic and diabetic subjects.

Example 3: Skin Samples from Diabetic Subjects have Lower Levels of Collagen and Elevated Levels of Cathepsin K FIGS. 3A-3B illustrate the expression levels of cathepsin K and collagen proteins in human diabetic and non-diabetic skin samples (courtesy, National Disease Research Interchange). The diabetic skin had significantly decreased collagen levels compared to nondiabetic skin and elevated levels of cathepsin K.

Western blot for collagen (A) and cathepsin K proteins in human skin from non-diabetic and diabetic subjects. A. Mean collagen expression levels were significantly lower in (*p<0.01) in the diabetic skin (n=7) compared to the non-diabetic skin (n=10). B. In contrast, cathepsin K levels were significantly elevated in (**p<0.001) in the diabetic skin.

Figure 4:
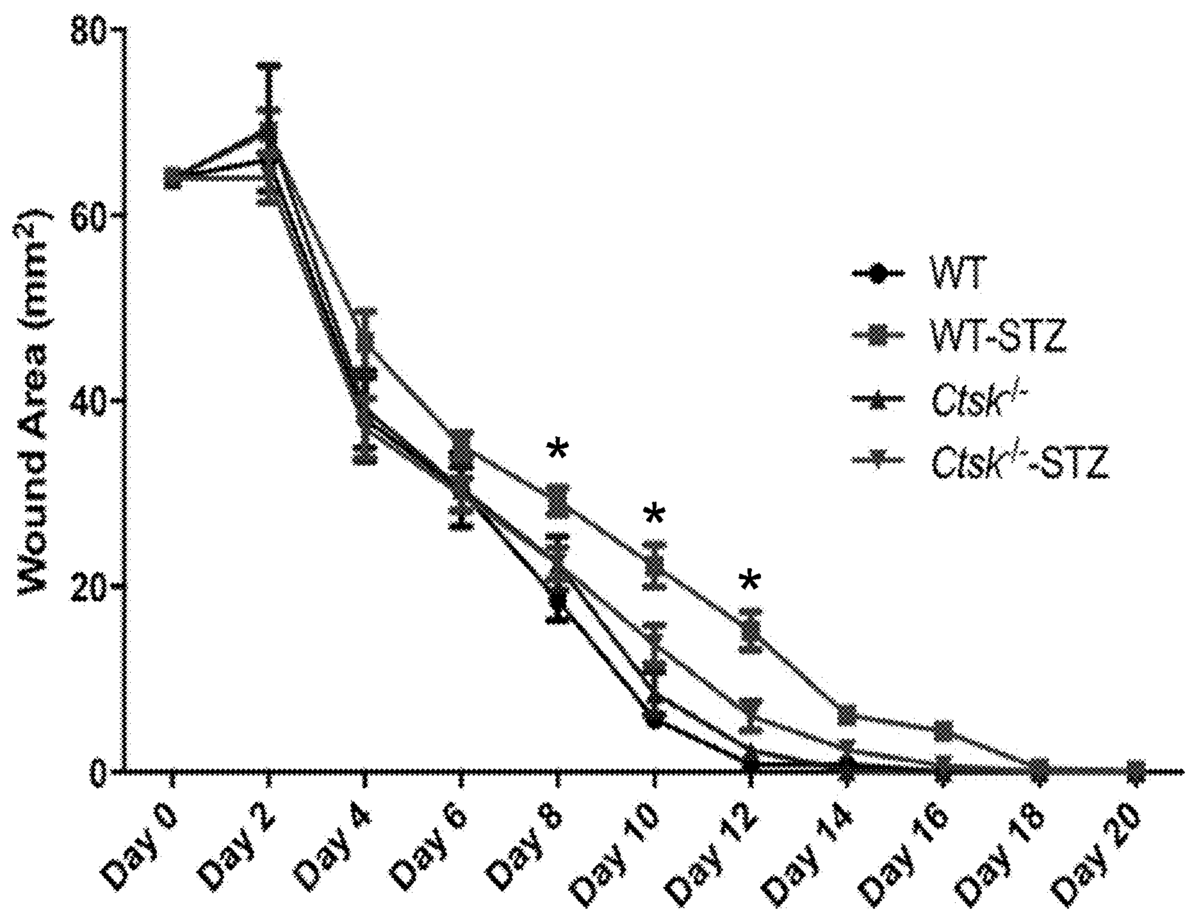
FIG. 4 depicts a graph comparing wound healing over time for WT and cathepsin K knockout mice in a chemically (streptozotocin)-induced diabetic model.

Example 4: Knockdown of Cathepsin K Gene Accelerates Wound Healing in Diabetic Mice FIG. 4 depicts the acceleration of wound healing in streptozotocin-induced diabetes in cathepsin K knockout mice compared to wild-type mice. Mice were rendered diabetic by subjecting them to intraperitoneal injection of streptozotocin (STZ). Four weeks after injection of STZ, a full thickness 8 mm excisional wound was created on the dorsum of the mice. As early as 8-days post wounding, cathepsin K knockout mice exhibited significant reduction in wound surface area as compared to the wildtype mice. Data obtained in this graph is the mean wound area from n=8-10 mice. It is pertinent to note that due to increased mortality of mice treated with STZ, additional mice numbers were included (over those determined by power analysis) in the STZ-treatment group and the experiment was repeated. Also, the mice treated with streptozotocin had severe weight loss and were very lean, which made the accurate assessment of wound dimension a challenge.

Figure 5:
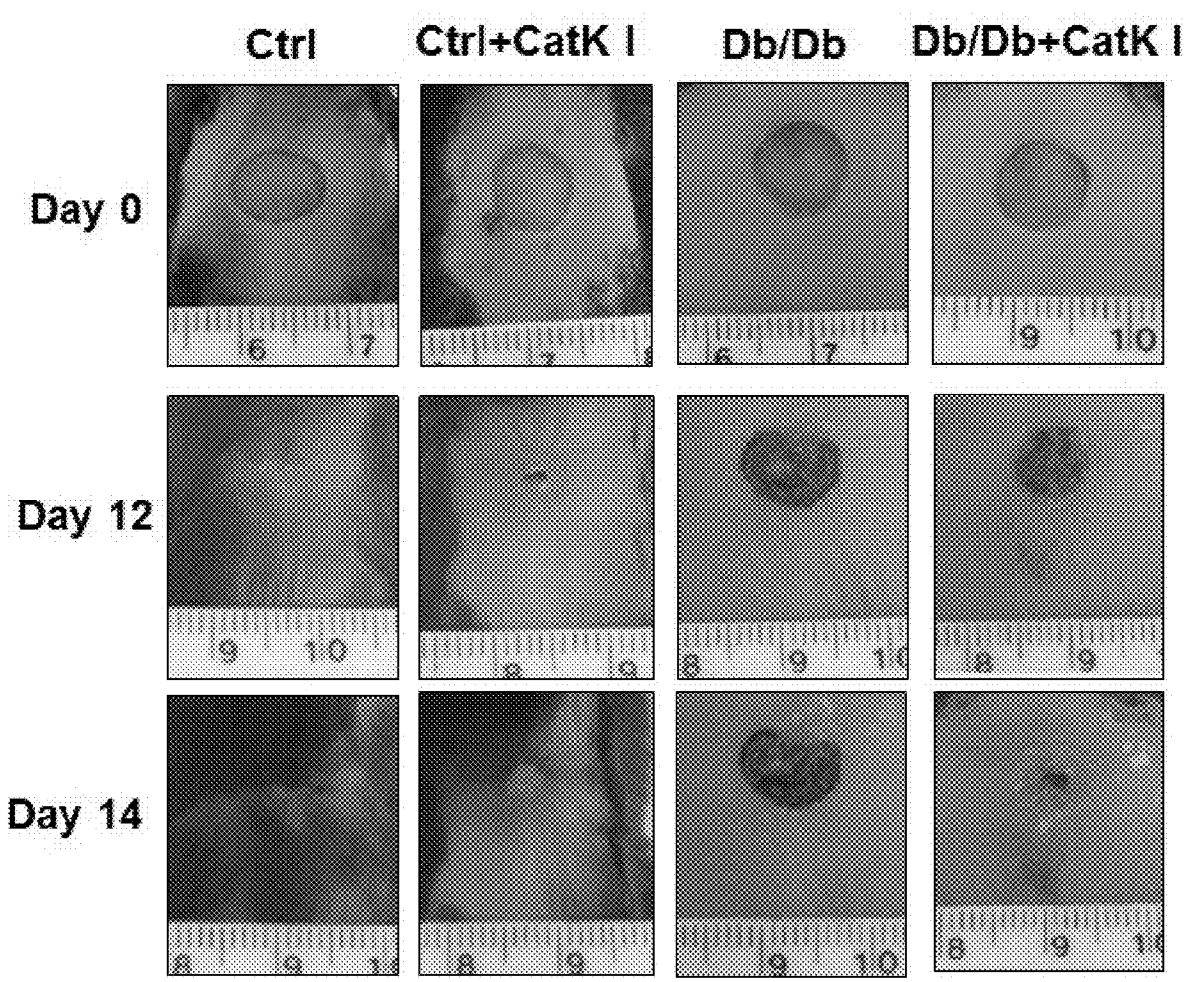
FIG. 5 shows images comparing wound healing in genetically diabetic (db/db) mice over time in response to treatment with vehicle and cathepsin K inhibitor.

Example 5: Pharmacological Inhibition of Cathepsin K Facilitates Wound Healing in Genetically Diabetic (Db/Db$^{+/+}$) Mice FIG. 5 illustrates the effect of a topically delivered pharmacological inhibitor of cathepsin K on wound healing in genetically diabetic mice. Excisional skin wounds were created in genetically diabetic db/db mice and the wounds were treated topically with cathepsin K inhibitor II or vehicle. Wound healing was evaluated by measuring the wound closure rate and histomorphometric analysis. As evidenced by FIG. 5 diabetic mice receiving the inhibitor exhibited significant resolution of wound by day 12 and by day 15 almost complete resolution was observed. In contrast, wounds in the vehicle treated group remain unhealed during this time period. Heterozygous (db/db$^{+/-}$) mice were used as controls in these studies.

Example 6: Further Evaluation of the Role of Cathepsin K in Diabetic Wound Healing Dysregulated cathepsin K in diabetic wound healing is modeled using recombinant cathepsin K. Exogenously applied cathepsin K impairment in diabetic wound healing is evaluated.

Using a clinically-relevant porcine model, the role of cathepsin K in diabetic wound healing is evaluated. Specifically, assessment is made of the causal relationship between increased cathepsin K and impairment in diabetic wound healing by attenuating collagen deposition, vascularization and granulation tissue formation.

The relationship between of cathepsin K levels and diabetic wound healing in a clinically relevant porcine model of diabetic wound healing is evaluated.

Anatomical and physiological similarities between pig and human skin make pigs an appropriate model for wound healing studies and have been extensively used in the literature. Like humans, pigs have a relatively thick epidermis with sparse hair growth and the skin is adherent to underlying structures (does not slides over the subcutaneous fascia). Additionally, the collagen type and the turnover time of the pig epidermis (30d) is approximately similar to that of the human skin. Furthermore, the immune cells in skin of the pigs are similar to those in human skin. These characteristics make the pig model of wound healing and appropriate and relevant model to mimic human wound healing.

Using female domestic pigs, a diabetic phenotype is induced with Streptozotocin (STZ) injections. The animals are anesthetized with intramuscular injections of ketamine 10 mg/kg, xylazine 5 mg/Kg and acepromazine 0.2 mg/kg, followed by a complete general anesthesia induced by mask inhalation of 1-2% isoflurane. A central venous catheter is placed and streptozotocin is administered intravenously (150 mg/kg, 1 g STZ in 10 mL sodium citrate buffer freshly prepared, given over 10 min). To avoid hypoglycemia due to insulin released by the destroyed beta-cells, 200 mL of a 5% glucose solution is given over 1 h period after STZ injection. The diabetic phenotype develops within 4 weeks.

Following induction of anesthesia, the dorsal skin of the pig is shaved, and each animal is reproducibly subjected to ten-full-thickness one-inch square excisional skin wounds (300 m thickness) using a scalpel. The wounds are spaced a minimum of 2-cm apart and in two columns on each side of the dorsal thoracolumbar midline. All wounds are dressed with an occlusive dressing. Wound photographs are taken immediately after wounding and on day 0, 7, and 14 with a camera mounted on a tripod at a fixed distance. Time to wound closure (# of days for complete reepithelialization) and % wound closure (1−[wound area/original wound area]) is determined. Imaging software calculates the wound area for each pig and measurements of changes over time.

Fifteen days after wounding the animals are euthanized with an overdose of sodium pentobarbital (100 mg/kg, intravenous). Wounds are harvested with at least 1-cm of surrounding healthy tissue at the depth of the muscle fascia and subject to analysis.

Epithelial gap, granulation tissue, vascularization, and collagen content is assessed. Deparaffinized skin-tissue sections are stained with H&E and are analyzed for the epithelial gap (distance between the advancing edges of keratinocyte migration and granulation tissue). Vascularization is detected by staining with CD31 antibody. Collagen content is determined by staining the section with Picro-Sirius and total ECM content is analyzed by Mason-Goldner trichome staining.

Tissue analysis is performed and mRNA and protein levels of cathepsin K is determined by quantitative RT-PCR and Western analysis respectively. Cathepsin K activity is determined using a fluorescence-based assay (Abcam). For immunohistochemical detection of cathepsin K, tissue sections are probed with anti-cathepsin K antibody followed by Alexa-Fluor-594 AffiniPure donkey anti-rabbit IgG.

Wound inflammation, proinflammatory cytokine and oxidative stress is assessed. Wound tissues are homogenized, sonicated, centrifuged and supernatants will be subjected to multiplex ELISA for different cytokines (BioRad, Bioplex-Pro). Specifically, the levels of IL-6, TBF□1, and VEGF will be determined. The levels of malondialdehyde and the activities of GSH-Px and catalase in the wounds are determined.

Example 7: Dysregulated Cathepsin K in Diabetic Wound Healing May be Ameliorated Using Cathepsin K siRNA Knockdown of cathepsin K using siRNA may be used to facilitate wound closure and promote healing of diabetic wounds.

Previous studies have shown that an n=8-10 wounds are sufficient to declinate statistically significant differences in wound healing (Singer and McClain, S. A. *Acad Emerg Med.* 10: 1029-33, 2003; Long, et. al, *J Control Release* 253: 73-81, 2017; Hamed et. al. *Diabetes.* 66: 2254-65, 2018). We have six groups collectively for Example 6 & 7: 1) Vehicle for streptozotocin (STZ) 2) STZ-treated 3) STZ+ vehicle for recombinant cathepsin K 4) STZ+ recombinant cathepsin K 5) STZ+scrambled siRNA and 6) STZ+cathepsin K siRNA. Previous studies have shown that an n=8-10 wounds are sufficient to declinate statistically significant differences in healing. Consequently, 6 pigs (a sample size of 60 wounds) are assessed in the study.

This study involves three experimental groups—five STZ-treated pigs each of the following groups: cathep sin K inhibitor, cathepsin K siRNA, and miR-146a. Anesthesia is induced as described using ketamine, xylazine, and acepromazine injection. Following induction of anesthesia, the dorsal skin of the pig is shaved, depilated and prepped with chlorhexidine or betadine. Each animal is reproducibly subjected to ten full-thickness skin wounds one-inch square wounds (~300-micrometer thickness) using a scalpel. The wounds are spaced a minimum of two centimeters apart and created in two columns on each side of the dorsal thoracolumbar midline. Wounds are treated with intradermal injections (using a Hamilton Syringe) of either 50 μl vehicle (phosphate buffered saline) or 10 μM solution of cathepsin K inhibitor II in DMSO+PEG (20:80) or scrambled or cathepsin K siRNA (200 pico g) liposomes. All wounds are dressed with an occlusive dressing (Tegaderm; 3M, St. Paul, Minn.). Wound photographs are taken immediately after wounding and on day 0, 7, and 14, with a camera mounted on a tripod at a fixed distance. Animals also receive additional doses of the treatment at the same time. Animals are anesthetized prior to taking pictures. On day 15 following wounding, animals are euthanized with an overdose of sodium pentobarbital (100 mg/kg) administered intravenously. The wounds will be harvested with at least 1 cm of surrounding healthy tissue at the depth of the muscle fascia and will be used for analysis.

Agarose siRNA liposomes are formulated. A 1% sterilized stock solution of low-melting-point agarose VII is diluted to 0.4% (w/v) using prepared siRNA-liposomes complexed with Lipofectamine-2000 (ratio of 600 pmol siRNA to 0.5 mL lipofectamine). As a marker for skin penetration, a fluorophore-tagged siRNA, siGLO Red is included in the siRNA-liposomal complex.

One pig is used for each vehicle, recombinant cathepsin K, scrambled siRNA, and cathepsin K siRNA treatments (total of four pigs). Wounding is done as described in Example 6. Recombinant cathepsin K (50 μL of 20 μg/mL) is applied topically to the wounds in a radial pattern using a Hamilton syringe on a daily basis. For siRNA studies, 200 pmol cathepsin K siRNA or 200 pmol scramble siRNA in the liposomal formulation is applied to the wounds (in a total volume of 10 μL) immediately after wounding and once every 3 days. Pigs are anesthetized with isoflurane on days 3, 9, and 12 and wounds are photographed. Time to wound closure epithelial gap, granulation tissue, vascularization, collagen content and cathepsin K levels are analyzed as described above.

In non-diabetic pigs the time to wound closure, a definitive measure of complete reepithelialization is ~12-14 days whereas diabetic pigs generally take a longer (~21 days). Evaluation of a reciprocal relationship between wound cathepsin K levels and collagen is assessed. The comparative healing time for wounds treated the pharmacological inhibitor or cathepsin K siRNA to exhibit complete re-epithelization is assessed. Additionally, increases in neovascularization and increases in granulation tissue in the animals receiving cathepsin K inhibitor and siRNA is compared.

An important role of cathepsin K diabetic wound healing is assessed and siRNA mediated knockdown of cathepsin K to accelerate diabetic wound healing by increasing wound collagen content, reducing inflammation, enhancing wound angiogenesis and re-epithelization of the wound. Diminished cathepsin K levels in the wound may facilitate wound healing.

Further assessment of cathepsin K and/or compensatory upregulation of other cathepsins or proteases including MMPs (MMPs are known to be cleaved and regulated by cathepsin K) are assessed by measuring levels of other key cathepsins and MMPs in the diabetic wound. Also, cystatin C, the endogenous inhibitor of cathepsin K may be upregulated in response to exogenous cathepsin K, and measures for cystatin C are included.

The efficacy of the siRNA and recombinant cathepsin K may be measured or modulated. Previous studies have shown that a 50% reduction in reporter gene may be required to produce therapeutic effects for other skin disorders. The addition of a chemical penetration enhancer, such as propylene glycol or commercially available Accell™-siRNA may be used to enhance cellular uptake and improve the efficacy of gene silencing.

Example 8: Evaluation of Mechanisms of Action

Without wishing to be bound by theory, the mechanisms of action of targeting cathepsin K in wound healing are discussed. Mechanisms by which targeting cathepsin K facilitates wound healing involve cell types in the diabetic wound that express cathepsin K.

The inventor's research has produced a cardiomyocyte-specific cathepsin K knockout mice knockout using the Cre-Lox system and found that this conditional knockout protects against doxorubicin-induced cardiotoxicity. Using the whole-body knockout of cathepsin K and conditional knockouts of cathepsin K. A conditional knockout of cathepsin K using the Cre-Lox system can be used to knockout cathepsin K in selective cell types.

Additionally, upstream signals (proinflammatory cytokines, oxidative stress) and downstream effectors of cathepsin K are relevant. Oxidative stress causes the release of cathepsin K from the lysosomes of cardiomyocytes which subsequently cleaves and activates caspases, causing apoptosis. Similar pathways in wound tissue may be relevant. The stromal-derived factor (SDF-1α) is an important regulator of epidermal cell migration and angiogenesis associated with wound repair. In neuroblastoma cells, SDF-1α serves as a substrate for cathepsin K. Lower levels of SDF-1α may be associated with a reciprocal increase in cathepsin K in wound samples from diabetic mice (data not shown). Primary neonatal human epithelial keratinocytes and diabetic human adult epithelial keratinocytes may be used to further explore the mechanisms by which cathepsin K regulates wound healing.

Example 9: Approaches to Targeting Endogenous Cathepsin K

Cathepsin K is a cysteine protease with potent collagenolytic and elastolytic activity. It is unique among collagenases in its ability to cleave type I collagen. Cathepsin K is highly expressed in dermal fibroblasts of surgical scars, while its levels are quite low in the normal skin. Although cathepsin K is localized in the lysosomes, the inventor's research has shown that cathepsin K translocates to the cytoplasm under conditions of cellular stress. Recent studies have attempted the modulation of matrix metalloproteases and neutrophil elastases to aid in wound healing. However, unlike matrix metalloproteases and neutrophil elastases, cathepsin K can function both as an extracellular collagenase that can break down ECM, and an intracellular collagenase that can degrade endocytize collagen, which renders it a more attractive target. Methods are provided for inhibition of cathepsin K to prevent the degradation of collagen in the wounds and thereby facilitate wound healing.

Microinjection of a pharmacological inhibitor of cathepsin K is a method to facilitate wound healing.

Inhibition of gene expression via topical administration of cathepsin K siRNA is a method to facilitate wound healing. Once inside the cell, the topically administered siRNA degrades its endogenous mRNA, thereby knocking down the target gene for post-transcriptional gene silencing and treating diabetic wounds. The siRNA molecules can achieve >80% target protein inhibition at nanomolar concentrations, and their enhanced intracellular stability enables knockdown that can last for weeks in nondividing cells. Moreover, the silencing is transient and local, alleviating concerns of prolonged action and off-target effects. Delivery methods to enhance penetration of the skin, provide effective mechanisms for sustained delivery, and overcome negative charge of the wound, increase efficacy for topical siRNA. To overcome these issues, methods are provided using a topical agarose matrix-based siRNA delivery system that reproducibly delivers siRNA into the skin tissue. This technique has been successfully used to silence several proinflammatory genes (e.g. p53, Smad3, Keap1, nrf2) and to promote remodeling and wound closure.

Cathepsin K is overexpressed in the inflamed skin, particularly in skin fibroblasts and keratinocytes. Methods of treatment are provided for inhibiting this potent, proinflammatory protease to facilitate diabetic wound healing.

According to the embodiments described herein, a topical agarose matrix-based formulation can be used to deliver cathepsin K siRNA to the diabetic wound. The use of siRNA in treating diabetic wounds has many potential advantages. Using siRNA to target cathepsin K can also be extended to treat related conditions such as pressure ulcers, infections, burns, lower limb ulcers due to venous stasis, and age-related ulcers.

According to the embodiments described herein, a wound dressing may be adapted to deliver an agent that degrades cathepsin K, an agent that inhibits the proteolytic action of cathepsin K, or an agent that inhibits the expression of cathepsin K. The agent may include a siRNA and antisense oligonucleotide. The dressing may include a bandage, a porous support structure, a biocompatible, biodegradable polymer, a hydrocolloid, a gel matrix, or the like.

According to the embodiments described herein, a method for treating a wound in a subject in need thereof, comprises administering a therapeutic composition comprising: an agent that degrades cathepsin K, an agent that inhibits the proteolytic action of cathepsin K, or an agent that inhibits the expression of cathepsin K.

In some embodiments, the subject has diabetes. In some embodiments, the subject has a chronic wound.

In some embodiments, the agent is a siRNA.

In some embodiments, the agent is a protease inhibitor.

In some embodiments, the agent is a cathepsin K selective inhibitor.

In some embodiments, the agent is odanacatib.

In some embodiments, the composition may be applied as a liquid, a gel, a cream, an ointment, a dry adhesive coating, an aerosol, a dry aerosol, a pump spray, a film, a salve, a semi-gel, a foam, a paste, a suspension, an ointment, an emulsion, or a powder.

In some embodiments, the composition may be applied directly to a wound or to a wound-contacting delivery vehicle, such as a suture or wound dressing. A wound dressing may include a bandage, a pad, a medical compress, a medicated sponge, a surgical patch, a hemostatic fleece, a hemostatic pad, a surgical dressing, a wound packing, a swab, or a gauze.

In some embodiments, the composition further comprises one or more anti-inflammatory agent, immunosuppressive agent, immunomodulatory agent, anti-microbial agent, anti-viral agent or a combination thereof.

In some embodiments, the composition further comprises a matrix metalloproteinase (MMP), fibrinogen, thrombin, factor XIII, hydrocolloid, collagen, cellulose, chitosan, zeolite, or calcium.

In some embodiments, the composition is administered topically, intradermally, subcutaneously, intravenously, or orally.

In some embodiments, the method further comprises, promoting production of collagen in the ECM.

In some embodiments, the method further comprises, administering a protease inhibitor to the wound or adjacent tissue.

In some embodiments, the levels of cathepsin K are measured and the composition is applied if levels of cathepsin K are elevated. In some embodiments, the levels of cathepsin K are measured and the composition is not applied if levels of cathepsin K are not elevated. In some embodiments, measuring levels of cathepsin K is performed more than one day after a wound is sustained or a surgery performed. In some embodiments, measuring levels of cathepsin K is performed between 1-20 days or between 2-15 days after a surgery. In some embodiments elevated levels of cathepsin K are higher by 50% or greater than in a tissue sample from a non-diabetic control. In some embodiments elevated levels of cathepsin K are 25%-100% greater in a sample from a wound than in a non-injured tissue sample from the same subject. In some embodiments elevated levels of cathepsin K are identified if cathepsin K mRNA levels measured in a sample from a wound in a subject, as compared with cathepsin K mRNA levels measured in a control sample from a wound from a non-diabetic control, are between 50%-1000% greater in the sample relative to the control. In some embodiments elevated levels of cathepsin K are identified if cathepsin K mRNA levels are more than twice that of a control.

In some embodiments, the composition is applied to a wound exhibiting delayed healing. In some embodiments, the composition is applied to a wound is associated with diabetes mellitus, pressure necrosis, or vasculitis.

In some embodiments, the composition is applied to a pressure ulcer, an infection, a burn, a lower limb ulcer associated with venous stasis, an area of neuropathic pain, an arthritic area, or an age-related ulcer.

In some embodiments, a method of treating a wound comprises: delivering a therapeutic composition to a subject in need thereof, wherein the therapeutic composition comprises an agent that degrades cathepsin K, an agent that inhibits the proteolytic action of cathepsin K, or an agent that inhibits the expression of cathepsin K. In some embodiments, the composition is applied to a wound in a diabetic patient undergoing surgery. In some embodiments, the composition is applied to a surgical wound immediately prior to suturing the wound. In some embodiments, the composition is applied to a surgical wound immediately after to suturing the wound. In some embodiments, the composition is applied to a surgical wound in a diabetic patient when applying a wound dressing. In some embodiments, the subject is a diabetic surgical patient, wherein the subject has a medical history of delayed wound healing.

Pharmaceutical Compositions

For administration to an animal or a human, the therapeutic compounds or molecules of the present invention are combined with an acceptable carrier to form a pharmaceutical composition and are administered to the animal or the human. The therapeutic compounds of the present invention may be reconstituted in any pharmaceutically acceptable carrier before use or administration.

Pharmaceutically Acceptable Carriers

In general, the nature of the carrier will depend on the particular mode of administration being employed. For instance, carrier formulations may include pharmaceutically and physiologically acceptable fluids such as water, physiological saline, balanced salt solutions, aqueous dextrose, glycerol or the like as a vehicle. The composition may include gelling agents, emulsifying agents and the like. In addition to biologically-neutral carriers, pharmaceutical compositions to be administered can contain minor amounts of non-toxic auxiliary substances, such as wetting or emulsifying agents, preservatives, suspending agents, thickening agents, anti-oxidants, buffers, bacteriostats, and pH buffering agents and the like, for example sodium acetate or sorbitan monolaurate. In yet another embodiment, the pharmaceutical compositions can be delivered in a controlled release system. Combinations of administration methods may also be employed.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein, including those for use in treating disorders, for example skin disorders, may be administered locally to a wound and adjacent area by administration routes, such as subcutaneous, intradermal, and topical. They may be administered in different forms, including but not limited to solutions, emulsions and suspensions, microspheres, particles, microparticles, nanoparticles, and liposomes. In one embodiment, therapeutic compounds are combined with an acceptable carrier to form a pharmaceutical composition for topical administration to a wound site.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation should be decided according to the judgment of the health care practitioner and each subject's circumstances.

The pharmaceutical compositions of the present disclosure can be administered in a single dose application, at about the same dose throughout a treatment period, in an escalating dose regimen, or the dose may be varied during the course of a treatment based on the condition of the subject being treated, the severity of the disease or condition, the apparent response to the therapy, and/or other factors as judged by one of ordinary skill in the art.

The terminology used herein is for the purpose of describing particular example embodiments only and is not intended to be limiting. It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed. Individual elements or features of a particular embodiment are generally not limited to that particular embodiment, but, where applicable, are interchangeable and can be used in a selected embodiment, even if not specifically shown or described.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for treating a skin wound in a diabetic subject in need thereof, comprising:

administering a therapeutic composition comprising: an agent that degrades or inhibits cathepsin K, wherein the agent comprises cathepsin K inhibitor II or siRNA that has a sequence that is complementary to a nucleic acid sequence encoding cathepsin K;

wherein:

the composition is administered topically, intradermally, or subcutaneously to the skin wound.

2. The method of claim 1, wherein the skin wound is on a lower limb of the diabetic subject.

3. The method of claim 1, wherein the skin wound is a chronic wound.

4. The method of claim 1, wherein the agent is a siRNA that has a sequence that is complementary to a nucleic acid sequence encoding cathepsin K, and wherein the composition comprises an agarose matrix-based media.

5. The method of claim 1, wherein the agent is cathepsin K inhibitor II.

6. The method of claim 1, wherein the composition is provided in a medical compress, a medicated sponge, a surgical patch, a dry adhesive coating, an aerosol, a dry aerosol, a pump spray, a film, a hemostatic fleece, a hemostatic pad, a gauze, a salve, a semi-gel, a gel, a foam, a paste, a suspension, an ointment, an emulsion, a moldable form, a surgical dressing, a wound packing, or a swab.

7. The method of claim 1, wherein the composition further comprises one or more anti-inflammatory agent, immunosuppressive agent, immunomodulatory agent, anti-microbial agent, anti-viral agent or a combination thereof.

8. The method of claim 1, wherein the composition further comprises a matrix metalloproteinase (MMP), fibrinogen, thrombin, factor XIII, hydrocolloid, collagen, cellulose, chitosan, zeolite, or calcium.

9. The method of claim 1, further comprising: administering the composition to the skin wound and adjacent tissue.

10. A dermal wound dressing comprising:

a porous support structure; and a therapeutic composition comprising: an agent that degrades or inhibits cathepsin K comprising cathepsin K inhibitor II.

11. The dressing of claim 10, wherein the composition is provided in a medical compress, a medicated sponge, a surgical patch, a dry adhesive coating, an aerosol, a dry aerosol, a pump spray, a film, a hemostatic fleece, a hemostatic pad, a gauze, a salve, a semi-gel, a gel, a foam, a paste, a suspension, an ointment, an emulsion, a moldable form, a surgical dressing, a wound packing, or a swab.

12. The dressing of claim 10, wherein the composition further comprises one or more anti-inflammatory agent, immunosuppressive agent, immunomodulatory agent, antimicrobial agent, anti-viral agent or a combination thereof.

13. The dressing of claim 10, wherein the composition further comprises a matrix metalloproteinase (MMP), fibrinogen, thrombin, factor XIII, hydrocolloid, collagen, cellulose, chitosan, zeolite, or calcium.

* * * * *